(12) United States Patent
Kreisler et al.

(10) Patent No.: US 8,191,806 B2
(45) Date of Patent: Jun. 5, 2012

(54) METHODS FOR ENHANCED PROCESSING OF BIOMASS USING FLASH DESICCATION AND/OR MECHANICAL HYDRODYNAMIC CAVITATION

(75) Inventors: Kevin Elliot Kreisler, Mt. Arlington, NJ (US); David James Winsness, Alpharetta, GA (US)

(73) Assignee: GS Cleantech Corporation, New York, NY (US)

( * ) Notice: Subject to any disclaimer, the term of this patent is extended or adjusted under 35 U.S.C. 154(b) by 234 days.

(21) Appl. No.: 12/720,073

(22) Filed: Mar. 9, 2010

(65) Prior Publication Data

US 2010/0224711 A1 Sep. 9, 2010

Related U.S. Application Data

(60) Provisional application No. 61/158,516, filed on Mar. 9, 2009.

(51) Int. Cl.
*B02C 19/00* (2006.01)

(52) U.S. Cl. .................. 241/1; 241/21; 241/29
(58) Field of Classification Search .................. 241/1, 5, 241/21, 29, 39, 152.2, 301
See application file for complete search history.

(56) References Cited

U.S. PATENT DOCUMENTS

| 6,517,015 | B2* | 2/2003 | Rowley, Jr. ........... 241/5 |
| 6,715,705 | B2* | 4/2004 | Rowley, Jr. ........... 241/5 |
| 6,971,594 | B1 | 12/2005 | Polifka |
| 7,667,082 | B2 | 2/2010 | Kozyuk |

* cited by examiner

*Primary Examiner* — Mark Rosenbaum
(74) *Attorney, Agent, or Firm* — Cantor Colburn LLP

(57) ABSTRACT

Methods are disclosed for conditioning biomass. The methods generally include flash dessicating the biomass to reduce a particle size of the biomass; mixing the biomass with a liquid carrier; and exposing the biomass and the liquid carrier to a mechanical hydrodynamic cavitation process. The methods can be employed during ethanol production from grain based feedstock.

10 Claims, 1 Drawing Sheet

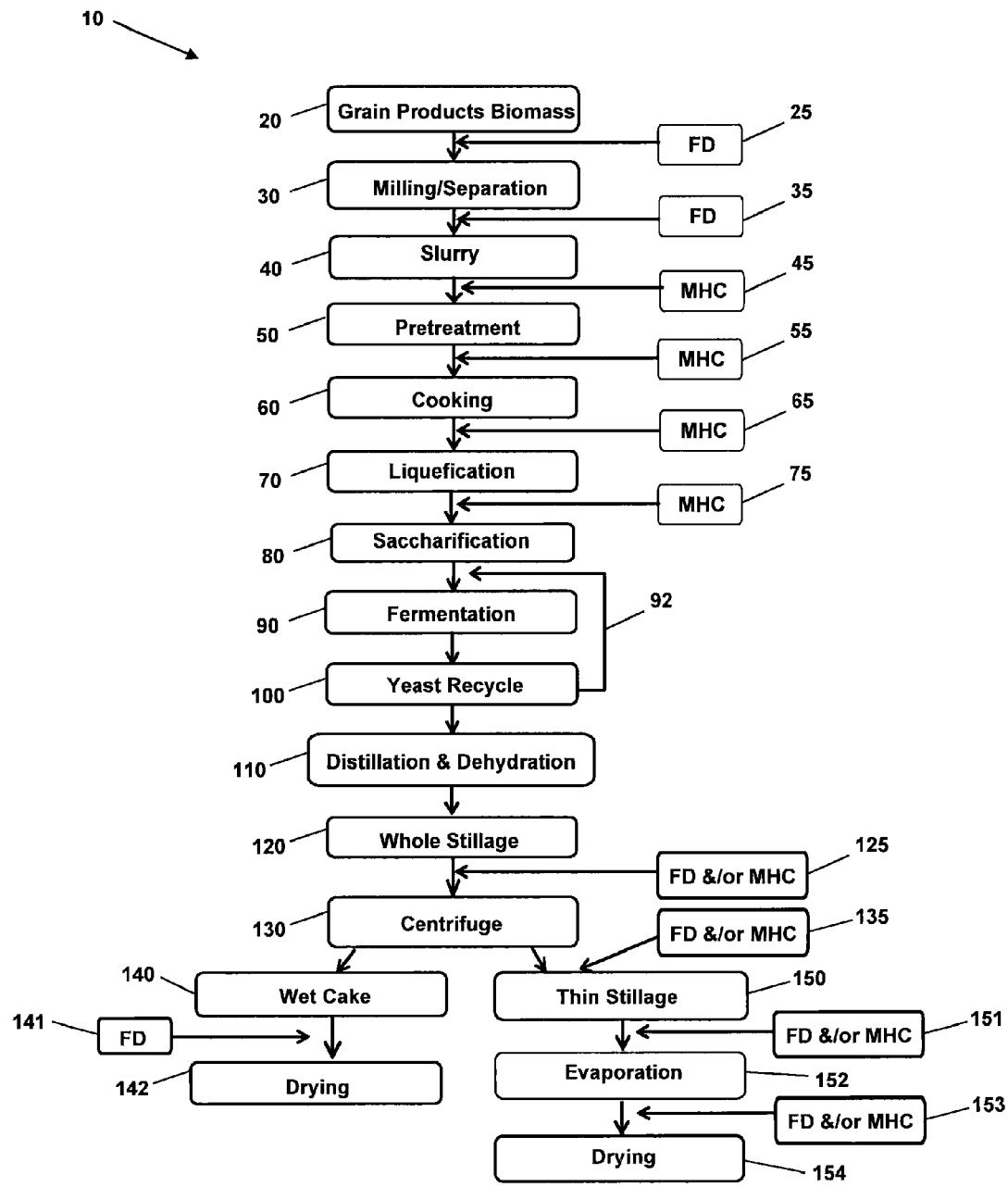

METHODS FOR ENHANCED PROCESSING OF BIOMASS USING FLASH DESICCATION AND/OR MECHANICAL HYDRODYNAMIC CAVITATION

CROSS REFERENCE TO RELATED APPLICATIONS

The present application relates to and claims priority to U.S. Provisional Application No. 61/158,516 filed on Mar. 9, 2009, incorporated herein by reference in its entirety.

BACKGROUND

The present disclosure generally relates to the methods for enhanced processing of cellulosic biomass and other forms of biomass using flash dessication and/or mechanical hydrodynamic cavitation.

Over the past thirty years, significant attention has been given to the production of ethyl alcohol, or "ethanol," for use as an alternative fuel. Ethanol not only burns cleaner than fossil fuels, but also can be produced using renewable sources such as corn, corn stover, corn cobs, switch grass forestry products, and the like.

Ethanol can be produced from various grains such as corn by either a wet milling or a dry mill process. In the wet milling process, the corn kernel is separated into different components such as germ, starch, protein, and fiber, resulting in several co-products. For example, separated germ is further processed for fat recovery; starch is saccharified and fermented for ethanol production; and protein and fiber can be used as feed material. In a traditional dry mill process, the corn is not fractionated and only two co-products are generally produced in addition to ethanol, Distillers Grains and $CO_2$. In this process, corn is ground and processed through fermentation and distillation, where the end products are ethanol, whole stillage and $CO_2$. The whole stillage contains water, a portion of starch that was not fermented, and the remaining non-fermentable portions of the kernel of corn such as protein, fiber, cellulose and hemicellulose corn fat and ash. Water is then removed from the whole stillage to form the dried distillers grains. At present, an estimated one hundred and fifty "dry milling" plants are producing over six billion gallons of ethanol per year. Additional plants presently idle or under construction are expected to add more than three billion gallons to this total.

While most of the ethanol production facilities currently in use are considered "dry milling", there has been a recent movement to build "fractionation-based" dry milling ethanol production facilities. These fractionated facilities attempt to separate as much of the non-fermentable portions of the grain as practical prior to the fermentation step. For example, corn kernels are comprised of three primary components: endosperm, germ, and bran. The endosperm contains the majority of the starch within the kernel of corn, or about 85%, whereas the germ and the bran contain high concentrations of non-fermentables (fiber, protein, and corn fat). Wet and dry fractionation technologies exist today that can be integrated into the dry milling process to effectively separate the endosperm, germ, and bran with minimal losses. The separated endosperm can then be conveyed to the fermentation process, and the germ and bran can then be sold directly to other markets and/or further processed.

With less non-fermentable mass entering the ethanol dry milling production process, greater volumes of ethanol can be produced per volume of fermentation capacity. In addition, separating non-fermentables prior to fermentation allows for a reduced mass of whole stillage exiting distillation and advantageously reduces energy loads on the whole stillage dehydration equipment. The downside of current technology is that the separation equipment and processes used need improvements to make the processes economically viable. For example, some of the starch exits with the non-fermentable components, thereby increasing the mass of corn required per volume of ethanol produced.

In both traditional dry milling and fractionated dry milling corn ethanol production facilities, the whole stillage is typically dehydrated by separating the heavy phase from the lighter phase using a centrifuge. The heavier phase is referred to as wet distillers grains and the lighter phase is referred to as thin stillage. The thin stillage is concentrated efficiently using multi-effect evaporation to produce a product referred to as condensed distillers solubles. Fat recovery methods are currently available to extract oil from the resulting co-products.

As the majority of United States derived biofuels are produced from grain, there needs to be continued focus to integrate new technologies that allow for more efficient conversion of grain to ethanol to allow for increased output relative to the same mass of grain inputs.

While the majority of ethanol produced in the United States is from grain, particularly corn, there remains a need to produce ethanol from alternative cellulosic feedstocks to offset the need for the various grains while allowing reduced dependence on petroleum based fuels. Desirable alternative feedstocks include, without limitation, corn cob, corn stover, DDGS (Distillers Dried Grain with Solubles), bran from fractionated production facilities, and many other forms of cellulosic biomass or cellulose containing waste streams such as paper, trash and/or sewage sludge.

SUMMARY

Disclosed herein are methods for conditioning biomass. In one embodiment, the method for conditioning biomass comprises, in sequence, flash dessicating the biomass to reduce a particle size of the biomass; mixing the biomass with a liquid carrier; and exposing the biomass and the liquid carrier to a mechanical hydrodynamic cavitation process.

In another embodiment, the method for conditioning biomass during ethanol production comprises flash dessicating the biomass prior to mixing the biomass with water to form a slurry in an amount effective to reduce particle size; and exposing the slurry to a mechanical hydrodynamic cavitation process.

In yet another embodiment, a distillation method for conditioning remaining solids, comprises flash dessicating the remaining solids and/or subjecting the remaining solids to a mechanical hydrodynamic cavitation, wherein the remaining solids are in a whole stillage feed stream, or a thin stillage feed stream, or a concentrated thin stillage feed stream, or a wet distillers grains with solubles.

The disclosure may be understood more readily by reference to the following detailed description of the various features of the disclosure and the examples included therein.

BRIEF DESCRIPTION OF THE DRAWINGS

The FIGURE schematically illustrates a process for production of ethanol from biomass in accordance with various embodiments of the present invention.

DETAILED DESCRIPTION

Disclosed herein are processes for conditioning of cellulosic and other forms of biomass for more efficient production of biofuel, feed, and other value-added products. The technology is designed to dramatically improve the energy balance and yield from biomass such as corn (and any derivative thereof), cellulose and other forms of biomass including, without limitation, grains, seeds, grasses, wood, algae, agricultural wastes, food wastes, forestry products, and waste products such as paper, trash and/or sewage sludge. As such, the biomass can be in the form of whole grains, grain derivatives such as starch and fiber, and cellulosic products such as corn cobs, corn stover, corn bran, distiller's dried grain with solubles ("DDGS"), switch grass, agricultural crop residue, yard waste, food wastes, forestry products, waste products such as paper, trash and/or sewage sludge. The conditioning generally includes flash dessication ("FD") and/or mechanical hydrodynamic cavitation ("MHC") the biomass at one or more of the processing steps that commonly occur during use of the biomass, e.g., during the production of ethanol from the biomass.

In FD, the biomass is subjected to compressed gas and/or super heated steam in a series of one or more enclosed cyclonic systems with no internal moving parts. The extreme thermal and/or pressure gradients have been found to almost instantly desiccate, shear, and atomize the biomass into fine particles. This process has been shown in prior experimentation with grain based and cellulosic biomass to produce particle sizes in the low micron levels with negligible impact on nutrient quality. The FD process has been shown in some cases to have altered the molecular structures of targeted grains and biomass. The output is a prepared powder having a substantially smaller particle size as compared to conventionally milled products. Importantly, the FD process renders the starch, hemicellulosic and lignocellulosic constituents of corn, corn cobs and stover far more available than any known conventional commercially available process. An exemplary flash dessication apparatus suitable for use in the present invention is shown and described in U.S. Pat. No. 6,971,594 B1 to Polifka, incorporated herein by reference in its entirety.

MHC provides cavitation by transmitting energy from rotating one or more rotor assemblies. One or more inline impeller-driven resonators with geometry optimized to induce violent inertial cavitation to disintegrate and reduce particles size of targeted particles disposed within a liquid. Liquids that are subjected to pressures below the liquid's saturated vapor pressure can overcome the liquid's intermolecular forces of cohesion and form cavities. These cavities, or cavitation bubbles, nearly instantly collapse due to the higher pressure of the surrounding liquid. This releases a significant amount of energy in the form of heat and an acoustic shock wave. Temperatures up to and exceeding 5,000 degrees Kelvin and pressures up to and exceeding 50 atmospheres give rise to the disintegration effect noted above. The effectiveness of cavitation increases with the presence of increased concentrations of smaller suspended solids because cavitation bubbles generally need a surface upon which they can nucleate. The output of FD is a large number of very small corn-mix particles that collectively provide a very large surface area and may enhance the productivity of MHC. MHC relies on mechanical and hydrodynamic phenomena to rapidly and cost-effectively generate highly energetic cavitation to disintegrate targeted biomass for nominal electricity (and carbon intensity) in a compact, continuous flow inline process.

As will be discussed herein, the MHC process can be after or independent of FD. The biomass is admixed with water and routed through a single or series of inline impeller-driven resonators with a geometry that induces violent inertial cavitation to disintegrate cellulosic and other targeted materials. Liquids that are subjected to pressures below the liquid's saturated vapor pressure can overcome the liquid's intermolecular forces of cohesion to form cavities. These cavities, or cavitation bubbles, nearly instantly collapse due to the higher pressure of the surrounding liquid. This releases a significant amount of energy in the form of heat and an acoustic shock wave. Temperatures up to and exceeding 5,000 degrees Kelvin and pressures up to and exceeding 50 atmospheres give rise to the disintegration effect noted above. The effectiveness of cavitation increases with the presence of increased concentrations of smaller suspended solids because cavitation bubbles generally need a surface upon which they can nucleate. The output of FD is a large number of very small particles that can collectively provide a very large surface area for MHC's cavitation bubbles to take hold. Transducer-based ultrasonication, which produces less energetic cavitation while consuming more electricity and requiring more infrastructure as compared to MHC, has been shown to give rise to material increases in the availability of fermentable sugar from whole corn, for example. MHC relies on mechanical and hydrodynamic phenomena to rapidly and cost-effectively generate far more energetic cavitation, which yields much better reaction kinetics for less electricity (and carbon intensity) in a compact, continuous flow inline process as compared to any transducer based process.

The FIGURE schematically illustrates an exemplary process 10 for conditioning the biomass 20 at one or more steps during an ethanol production process and is not intended to be limiting to processes for the production of ethanol. As will be described below, the FD and/or MHC may be integrated into a single step of the process or may be integrated into multiple steps of the process. As shown in step 30, the biomass is first milled. The milling step generally includes screening the biomass to remove debris and grinding the biomass into coarse particles, i.e., flour. Prior to or subsequent to milling, the biomass may be conditioned by FD steps 25 and/or 35, respectively. The FD step advantageously decreases the flour particle size that would normally be obtainable during a conventional milling process. Moreover, if FD occurs prior to milling, all of the biomass can be treated so as to increase the available biomass surface area for subsequent processing. Advantageously, reducing the particle size of the biomass by FD increases hydration efficiency since a larger surface area will be exposed during hydration.

In steps 40-90, the milled flour, with or without FD processing, is mixed with water to form a slurry and further processed to form a slurry mixture. After formation of the slurry in step 40, the slurry may be pretreated by adjustment of the pH and introduction of alpha enzymes such as alpha amylase. The slurry is typically heated at an elevated temperature during cooking step 60. During liquefaction step 70, the slurry is pumped through a pressurized cooker at a temperature greater than 212° F. for a relatively short period of time and quickly cooled by an atmospheric or vacuum flash condenser. The slurry is then maintained at an elevated temperature to permit the enzymes within the mixture to react with and break down the starch within biomass into shorter fragments such as maltodextrins and oligosaccharides. Additional enzymes such as gluco amylase may be added. The slurry mixture is then fed to the fermentation tanks, wherein the slurry mixture is often referred to as the mash. The additional enzymes that were previously added further break down the starch into simple sugars in the saccharification step 80. At each step detailed above, the slurry mixture may be subjected to an MHC process as is generally shown by step 45, 55, 65, and 75. The MHC processing can occur at a single step in the process or may occur multiple times at more than one step in the process. For example, the MHC process can occur only after pretreatment has occurred or may occur prior to pretreatment, and again, prior to cooking, and still again prior to liquefaction. The number and interval of MHC processing is not intended to be limited and will generally depend on the intended application of the conditioned biomass.

During fermentation step 90, yeast is added to convert the sugars within the mash into ethanol and carbon dioxide. The carbon dioxide can be released into the atmosphere or may be captured and purified with a scrubber so it can be marketed to the food processing industry for use in carbonated beverages and flash-freezing applications. The yeast may be added directly or may be recycled yeast as shown in step 100. The resulting mixture contains about 10-20% ethanol as well as the non-fermentable solids from the grain and added yeast.

In step 110, the ethanol is removed from the mixture by distillation leaving behind the non-fermentable byproducts. Typically, the distillation and subsequent dehydration of the ethanol occurs in a multi-column distillation system where additional heat is added to distill the ethanol from the mixture. By the time the product stream is ready to leave the distillation columns, it contains about 95% ethanol by volume and about 5% water. The product stream is then passed through a molecular sieve to physically separate the remaining water from the ethanol based on the different sizes of the molecules to produces anhydrous ethanol.

The non-fermentable residue from the distillation and dehydration step is referred to as whole stillage, which generally contains fiber, oil, protein, other unfermented components of the grain, yeast cells, and water. The whole stillage is isolated in step 120 and is subsequently centrifuged in step 130 to provide a wet cake 140 and thin stillage 150. In accordance with one embodiment, the whole stillage isolated in step 120 is subjected to the FD and/or the MHC process as shown in step 125 prior to being sent to the centrifuge so as to reduce the particle size of the solids contained therein.

The thin stillage typically has about 5 to 10 percent solids. Optionally, the thin stillage may be subjected to FD and/or MHC in step 135 as it exits the centrifuge. In some process flows, some of the thin stillage is recycled and used as process water at the front end of the process, e.g., added to form the slurry in step 40. The remaining thin stillage is concentrated through multiple evaporators as shown in step 152 to form syrup, i.e., a thin stillage concentrate. Prior to evaporation or subsequent to evaporation the thin stillage feed stream may be subjected to the FD processor the MHC process as shown in steps 151 and 153. The thin stillage syrup may then be further dried as shown in step 154. In some embodiments, the oil may be removed from the thin stillage syrup. A suitable process for removing the oil from the thin stillage 150 is disclosed in U.S. Pat. No. 7,601,858 to Cantrell et al., incorporated by reference in its entirety. In still other embodiments, the thin stillage concentrate is combined with the wet cake and further dried to reduce the total moisture content.

The wet cake, also referred to as distillers wet grains, can be used as feed or may be dried further to form dried distillers grains. A further drying step 142 provides an extended shelf life for the distillers grains such as may be desirable for use as animal feed. Prior to drying, the wet cake may be subject to the FD process as shown by step 141.

In another embodiment, the cellulosic forms of biomass such as those previously described can be milled and sized reduced by convention means and/or followed by FD prior to hydration. The hydrated product may then be further treated by: dilute or concentrated acid hydrolysis, enzymatic hydrolysis, steam explosion, autohydrolysis, ammonia fiber expansion, transducer based sonication, higher powered transducer sonication, MHC, or any combination thereof.

In another embodiment, FD may be applied post distillation to the whole stillage, thin stillage, syrup or WDGS (Wet Distillers Grains with Solubles). FD allows for rapid dehydration while minimizing damage to nutritional constituents.

In another embodiment, MHC may be applied post distillation to the whole stillage, thin stillage, partially evaporated thin stillage, syrup or WDGS.

In another embodiment, MHC may be applied to biomass slurry that has been pre or post treated by acid or dilute hydrolysis, ammonia fiber expansion, or steam explosion.

In another embodiment, MHC may be applied to hydrated biomass streams to reduce viscosity and improve flowability.

In another embodiment, MHC may improve reaction kinetics and reduce catalyst and/or enzyme requirements.

In another embodiment, MHC may be used to assist in neutralizing liquids and liquid slurries.

In another embodiment, MHC may be used to enhance the reaction kinetics of hydrolysis by, for example, admixing an acid into the biomass slurry prior to MHC processing, thus yielding even greater efficiencies in the breakdown of targeted cellulosic materials.

In yet another embodiment, corn oil is extracted from post distillation of ethanol.

The technology is designed to dramatically improve the energy balance and yield from corn (and any derivative thereof), cellulosic and other forms of biomass including, without limitation, grains, seeds, grasses, wood, algae, agricultural wastes, food wastes, forestry products, and waste products such as paper, trash and/or sewage sludge. A significant benefit of the technology is that it increases the availability of fermentable sugars and extractable lipids and protein in whole corn while enabling corn ethanol producers to diversify their feedstock mix by accepting and processing cellulosic biomass derived from corn (including corn cobs and stover) into additional ethanol, lipids and commercial feed products. For example, it is believed more starch is accessible to the enzymes by reducing the particle size using FD and/or MHC. This degree of flexibility does not exist in the corn ethanol industry today and it would enable existing corn ethanol producers to reduce their financial and market risk while enhancing their competitive posture in the growing but challenging renewable fuels industry. The technology is designed to achieve similar objectives for any enzymatic, thermal or other biomass-based production process such as cellulosic ethanol production by facilitating increased conversion efficiencies and diversification of feedstock and product mixes.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for conditioning biomass, comprising, in sequence:
   flash dessicating the biomass to reduce a particle size of the biomass;
   mixing the biomass with a liquid carrier; and
   exposing the biomass and the liquid carrier to a mechanical hydrodynamic cavitation process.

2. The method of claim 1, wherein the liquid carrier is water.

3. The method of claim 1, wherein the biomass comprises grains, cellulose, algae, wood, seeds, and grasses.

4. The method of claim 3, wherein the grains comprise corn.

5. A method for conditioning biomass during ethanol production, the method comprising:
    flash dessicating the biomass prior to mixing the biomass with water to form a slurry in an amount effective to reduce particle size; and
    exposing the slurry to a mechanical hydrodynamic cavitation process.

6. The method of claim 5, wherein exposing the slurry to the mechanical hydrodynamic cavitation process is immediately prior to a selected one or more of a pretreatment step, a cooking step, a liquefaction step, and a saccharification step.

7. The method of claim 5, wherein the biomass comprises grains, cellulose, algae, wood, seeds, and grasses.

8. The method of claim 5, wherein the flash dessicating the biomass prior to mixing the biomass with water to form the slurry is subsequent to milling of the biomass.

9. The method of claim 5, wherein the flash dessicating the biomass prior to mixing the biomass with water to form the slurry is prior to milling of the biomass.

10. The method of claim 5, wherein the flash dessicating the biomass prior to mixing the biomass with water to form the slurry is prior to and subsequent to milling of the biomass.

* * * * *